United States Patent
Han et al.

(10) Patent No.: US 9,120,735 B2
(45) Date of Patent: Sep. 1, 2015

(54) METHOD FOR PREPARING ACRYLIC ACID FROM PROPANE AND PROPYLENE

(75) Inventors: Scott Han, Lawrenceville, NJ (US); Christopher D. Frick, Pottstown, PA (US); Dmitri A. Kraptchetov, Lansdale, PA (US); Daniel J. Martenak, Perkasie, PA (US); Nelson I. Quiros, Houston, TX (US); Timothy J. Donnelly, Jamison, PA (US)

(73) Assignee: Rohm and Haas Company

( * ) Notice: Subject to any disclaimer, the term of this patent is extended or adjusted under 35 U.S.C. 154(b) by 0 days.

(21) Appl. No.: 14/351,404

(22) PCT Filed: Sep. 10, 2012

(86) PCT No.: PCT/US2012/054414
§ 371 (c)(1),
(2), (4) Date: Apr. 11, 2014

(87) PCT Pub. No.: WO2013/058888
PCT Pub. Date: Apr. 25, 2013

(65) Prior Publication Data
US 2014/0243554 A1    Aug. 28, 2014

Related U.S. Application Data

(60) Provisional application No. 61/548,372, filed on Oct. 18, 2011.

(51) Int. Cl.
*C07C 51/215* (2006.01)
*C07C 51/25* (2006.01)

(52) U.S. Cl.
CPC ............. *C07C 51/252* (2013.01); *C07C 51/215* (2013.01)

(58) Field of Classification Search
None
See application file for complete search history.

(56) References Cited

U.S. PATENT DOCUMENTS

| | | |
|---|---|---|
| 5,705,684 A | 1/1998 | Hefner et al. |
| 6,383,978 B1 | 5/2002 | Bogan, Jr. |
| 6,403,525 B1 | 6/2002 | Chaturvedi et al. |
| 6,407,031 B1 | 6/2002 | Chaturvedi et al. |
| 6,407,280 B1 | 6/2002 | Chaturvedi et al. |
| 6,461,996 B2 | 10/2002 | Chaturvedi et al. |
| 6,472,552 B1 | 10/2002 | Bogan, Jr. |
| 6,504,053 B1 | 1/2003 | Chaturvedi et al. |
| 6,589,907 B2 | 7/2003 | Chaturvedi et al. |
| 6,624,111 B2 | 9/2003 | Chaturvedi et al. |
| 6,653,253 B1 | 11/2003 | Lin |
| 6,812,366 B2 | 11/2004 | Lin |
| 7,253,311 B2 | 8/2007 | Nestler et al. |
| 7,304,014 B2 | 12/2007 | Cavalcanti et al. |
| 7,553,986 B2 * | 6/2009 | Bogan et al. ............ 558/319 |
| 7,807,853 B2 | 10/2010 | Dieterle et al. |
| 2007/0276157 A1 * | 11/2007 | Machhammer et al. ...... 562/545 |
| 2014/0243554 A1 | 8/2014 | Han et al. |

OTHER PUBLICATIONS

Grasselli et al. Catalysis Today (2010), 157(1-4), 33-38.*

* cited by examiner

*Primary Examiner* — Yong Chu
*Assistant Examiner* — Ana Z Muresan

(57) ABSTRACT

The application concerns a process comprising: (A) contacting a gas comprising oxygen, propane and propylene with at least one catalyst under reaction conditions sufficient to at least partially convert the propylene into a final product comprising acrylic acid; (B) feeding said final product to a separation column, in which the final product is split into a liquid stream, which is rich in acrylic acid, and a gaseous by-product stream comprising propane and propylene in a volume ratio of from 99.9:0.1 to 95:5; (C) contacting the gaseous by-product stream with oxygen in the presence of a catalyst under reaction conditions sufficient to at least partially convert propane to acrylic acid.

11 Claims, No Drawings

METHOD FOR PREPARING ACRYLIC ACID FROM PROPANE AND PROPYLENE

CROSS-REFERENCE TO RELATED APPLICATIONS

This application claims priority from provisional application Ser. No. 61/548,372, filed Oct. 18, 2011, which is incorporated herein by reference in its entirety.

BACKGROUND OF THE INVENTION

This invention relates to a process for producing α-, β-unsaturated carboxylic acids from off-gas and waste gas streams.

The current commercial process to produce acrylic acid uses a two-step process that first converts propylene to acrolein and subsequently converts acrolein to acrylic acid. An absorber tower, which in part separates the residual off-gas from the liquid product, typically immediately follows the reactor(s). This off-gas, called absorber off-gas (AOG), has a wide range of potential compositions but primarily contains unreacted gases from the oxidation reaction.

High purity chemical or polymer grade propylene currently is used as the feedstock to the commercial process. The cost of propylene, and in particular high purity propylene, is projected to increase significantly in the future, and economic incentives exist to use lower grade propylene streams, e.g. from FCC units in an oil refinery, to produce acrylic acid. However, the use of propylene streams containing higher levels of undesired propane creates a problematic situation for the AOG composition, which normally is sent to be processed as waste gas, e.g. sent to a thermal oxidizer. Issues such as: (1) loss of $C_3$ hydrocarbon to combustion, (2) generation of increased $CO_2$ waste gas, and (3) overloading of the thermal oxidizer, present difficulties in the use of propane-containing propylene feeds.

In addition, propane in the chemical grade propylene will not react with conventional catalysts used in the commercial manufacture of acrylic acid from propylene. The propane, however, takes up space in the reaction zone thus reducing the overall capacity of the reactor. Therefore, although there is an economic advantage to using the lower grade of propylene, there is a corresponding loss of capacity equivalent to the propane content of the propylene. Commercial chemical grade propylene may have as much as 7% by weight propane so the resulting capacity loss can be significant in a world-class oxidation train.

It would be desirable to have a modified conventional propylene process for producing carboxylic acids that could operate using low-purity propylene feedstocks. Furthermore, it would advantageous if the modified conventional process could be capable of converting unreacted propane in the AOG to acrylic acid product to reduce the negative impact of the capacity loss.

SUMMARY OF THE INVENTION

The invention is such a process comprising:
(A) contacting a gas comprising oxygen, propane and propylene with at least one catalyst under reaction conditions sufficient to at least partially convert the propylene into a final product comprising acrylic acid;
(B) feeding said final product to a separation column, in which the final product is split into a liquid stream, which is rich in acrylic acid, and a gaseous by-product stream comprising propane and propylene in a volume ratio of from 99.9:0.1 to 95:5;
(C) contacting the gaseous by-product stream with oxygen in the presence of a catalyst under reaction conditions sufficient to at least partially convert propane to acrylic acid It has surprisingly been found that a good yield of acrylic acid can be obtained by processing an AOG feed containing a low concentration of propane.

DETAILED DESCRIPTION OF THE INVENTION

The process involves oxidizing propylene to acrylic acid, and further involves oxidizing propane in the AOG to acrylic acid. The process can accomplish the propylene oxidation in one or two steps. The two-step process involves oxidizing propylene to acrolein, and oxidizing acrolein to acrylic acid. The one-step process comprises oxidizing propylene directly to acrylic acid. As mentioned hereinabove, chemical or polymer grade propylene commonly is used in the preparation of acrylic acid. The process of the present invention advantageously is able to use lower purity propylene-containing gases as a feed to the process. The process includes a finishing reactor to convert unreacted propane in the AOG to acrylic acid.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.).

Also herein, the recitations of numerical ranges and/or numerical values, including such recitations in the claims, can be read to include the term "about." In such instances the term "about" refers to numerical ranges and/or numerical values that are substantially the same as those recited herein.

For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

A high purity hydrocarbon feed is not necessary for the process disclosed herein. Mixtures of hydrocarbons may be purchased commercially, or may be obtained from commercial processes such as steam cracking and fluid catalytic cracking. A mixture of propylene and propane is the preferred hydrocarbon feedstock for the disclosed process. For example, without limitation, in the mixture of propane and propylene, the propane may be present in an amount of at least 0.1% by weight up to 95% by weight, preferably from 0.5% by weight to 10% by weight, or even 0.5% by weight to 5% by weight, based on the total weight of propane and propylene in the hydrocarbon feedstock.

An oxygen-containing gas provides molecular oxygen to the reaction system. The term "oxygen-containing gas," as used herein, refers to any gas comprising from 0.01% up to 100% oxygen, including, for example, air. While the oxygen-containing gas may be pure oxygen gas, it is usually more economical to use an oxygen-containing gas such as air, since 100% $O_2$ purity is not particularly required.

Suitable diluting gases include, but are not limited to, one or more of: carbon monoxide, carbon dioxide, nitrogen, argon, helium, and mixtures thereof. A suitable molar ratio of the starting materials for the initial feed gas (hydrocarbon):(oxygen):(diluting gas):($H_2O$), would be, for example, (1):(0.1 to 10):(0 to 20):(0.2 to 70), for example, including but not limited to, (1):(1 to 5.0):(0 to 10):(5 to 40).

Any suitable catalyst that may be used in the current 2-step propylene oxidation commercial process can be employed for the first and second reactions. A first catalyst can be used for the first reaction, namely converting propylene to acrolein, and a second catalyst may be employed for the second reaction, namely converting acrolein to acrylic acid. Alternatively, the propylene oxidation catalyst can be essentially the same catalyst for both the first and second reactions. Thus, the catalyst for the 2-step propylene oxidation may be the same or different for each step. The catalyst advantageously comprises a mixed metal oxide. As is well known in the art, the catalyst may be used alone, or may also be used together with a carrier, or support, such as, without limitation, silica, alumina, titania, aluminosilicate or diatomaceous earth. Further, the catalyst may be molded into a proper shape and/or particle size appropriate for the scale of the reaction system. The particular shape or geometry of the catalyst is not particularly limited in connection with the present invention. The selection of the catalyst, its shape, size and packing method are accomplished according to methods well known to persons having ordinary skill in the art. For example, suitable catalysts for a variety of vapor phase oxidation reactions are described fully in U.S. Pat. Nos. 6,383,978, 6,403,525, 6,407,031, 6,407,280, 6,461,996, 6,472,552, 6,504,053, 6,589,907 and 6,624,111. Many suitable catalysts are commercially available.

General conditions for the first and second reactions are as follows: the reaction temperature can vary from 200° C. to 700° C., but is advantageously in the range of from 200° C. to 550° C., for example, 300° C. to 450° C., or even 350° C. to 400° C.; the gas hourly space velocity in the vapor phase reactor is advantageously within a range of from 100 to 10,000 $hr^{-1}$, for example, 300 to 6,000 $hr^{-1}$, or even 300 to 2,000 $hr^{-1}$; the average contact time with the catalyst can be from 0.01 to 10 seconds or more, but is advantageously in the range of from 0.1 to 10 seconds, for example from 2 to 6 seconds; the pressure in the reaction zone advantageously ranges from 0 to 791 kPa guage (0 to 100 psig), such as, for example, no more than 446 kPa guage (50 psig).

In one embodiment of the invention, the propylene-to-acrylic acid conversion step may be achieved in a reactor system containing a catalyst that produces acrylic acid by propylene oxidation in a single step. Suitable catalysts are described fully in the prior art, such as U.S. Pat. Nos. 6,653,253 and 6,812,366.

The invention involves the use of a finishing reactor to produce acrylic acid by oxidizing propane that is present in the AOG. The finishing reactor is located downstream of the absorber. The feed to the finishing reactor may also include propane-containing gases from other process/waste gas sources.

The AOG waste gas composition is fed to the finishing reactor. This composition may vary according to the operation of the preceding reactor or reactors, but it advantageously comprises from 0.1 to 8 vol. % propane, preferably from 0.5% to 5%, based on the volume of gas fed to the finishing reactor.

The composition of the feed gas to the finishing reactor may be varied according to parameters known to those skilled in the art. For example, the feed stream(s) to the finishing reactor may be as follows: propane in an amount between 0.1 vol % and 8 vol %, such as between 1 vol % and 3 vol %, oxygen in an amount between 1 vol % and 50 vol %, such as between 5 vol % and 25 vol %, and water (steam) in an amount between 1 vol % and 50 vol %, such as 5 vol % and 25 vol %, based upon the total volume of the feed stream to the finishing reactor.

The catalyst used in the finishing reactor is a catalyst capable of converting propane to acrylic acid and can be a Mo/V/Te/Nb mixed metal oxide. Many suitable catalysts are commercially available. Examples of suitable catalysts are disclosed in U.S. Pat. No. 7,553,986.

The reaction system for the finishing reaction may be a fixed bed system or a fluidized bed system. For example, a fixed bed reactor using a shell and tube heat exchanger configuration with heat removal capability can be used. Another possible fixed bed system would be a simple adiabatic packed bed reactor, which has the advantage of lower cost. The target propane conversion conditions and the corresponding heat release expected can be used to determine the optimum reaction system configuration. In view of the fact that the reaction is an exothermic reaction, a fluidized bed system may be employed whereby it is easy to control the reaction temperature.

The propane oxidation in the finishing reactor can be run at conditions that maximize acrylic acid yield, and such conditions are well known to those skilled in the art. General conditions for the finishing reactor are as follows: the reaction temperature can vary from 200° C. to 700° C., but is advantageously in the range of from 200° C. to 550° C., for example, 300° C. to 450° C., or even 350° C. to 400° C.; the gas hourly space velocity in the vapor phase reactor is advantageously within a range of from 100 to 10,000 $hr^{-1}$, for example, 300 to 6,000 $hr^{-1}$, or even 300 to 2,000 $hr^{-1}$; the average contact time with the catalyst can be from 0.01 to 10 seconds or more, but is advantageously in the range of from 0.1 to 10 seconds, for example from 2 to 6 seconds; the pressure in the reaction zone advantageously ranges from 0 to 791 kPa gauge (0 to 100 psig), such as, for example, no more than 446 kPa gauge (50 psig).

In one embodiment of the invention, the exit gas from the finishing reactor can be combined with the exit gas of the main reaction stage to recover the acrylic acid thus formed. In one embodiment of the invention, the exit gas can be routed to the absorber tower directly. In one embodiment, the acrylic acid in the finishing reactor exit gas can be separated using any of several contact condenser designs capable of separating a gaseous product stream into multiple streams according to composition, such as separating a gaseous output stream into a first stream containing primarily the desired reaction product(s) and a second stream containing primarily unreacted materials and by-products. This by-product stream can be then sent, directly or combined with a suitable fuel gas, to a flare or thermal oxidizer for incineration. The acrylic-acid containing phase can be returned to the process or isolated for further purification after being adequately stabilized.

Optionally, the condensed phase from the finishing reactor can be stabilized with a polymerization inhibitor to protect it against undesirable fouling due to polymer formation. The polymerization inhibitor can be selected from phenols such as hydroquinone, substituted phenols, phenothiazine and its derivatives, 2,2,6,6-tetramethyl piperidin-1-oxyl stable free radical and its derivatives, dialkyl dithiocarbamate complexes of metal ions, such as copper ions, and other such compounds known to those skilled in the art of polymerization inhibition. Inhibitors can be used individually or in combination of two or more components or in combination with oxygen to effect improved inhibition performance.

The acrylic acid product from the finishing reactor can be combined with the acrylic acid product from the main propylene process, thus providing a yield benefit. The amount of additional acrylic acid product is dependent upon the propane feed concentration entering the finishing reactor.

Specific Embodiments of the Invention

The following examples are given to illustrate the invention and should not be construed as limiting its scope. All parts and percentages are by volume unless otherwise indicated.

EXAMPLES 1-5

The catalyst used in the finishing reactor was a high-performance Mo/V/Te/Nb mixed metal oxide prepared according to the procedure described in U.S. Pat. No. 7,304,014 B2, assigned to Rohm and Haas Company.

To simulate a typical AOG composition, a synthetic feed was used in the finishing reactor. Table 1 shows this representative AOG feed. As propane is the least reactive hydrocarbon species in the stream, propane was treated as the only reactive component in the model feed with $N_2$ as the balance. The other non-propane components in the feed are assumed to pass through the finishing reactor either untouched (such as $H_2O$, $CO_x$) or reacting analogously to a propane molecule.

TABLE 1

| Feed compositions | | |
|---|---|---|
| Component | Real Feed Molar Flow, mol % | Simulated Model Feed, mol % |
| $N_2$ | 69.4 | 72.0 |
| $H_2O$ | 25.8 | 25.6 |
| $CO_2$ | 1.36 | Inert |
| $C_3H_8$ | 0.651 | 0.651 |
| $C_3H_6$ | 0.156 | Inert |
| Acrolein | 0.204 | Inert |
| CO | 0.688 | Inert |
| Acrylic Acid | 0.120 | Inert |
| Acetic Acid | 0.0300 | Inert |
| Formaldehyde | 0.0100 | Inert |
| Acetone | 0.0082 | Inert |
| Acetaldehyde | 0.0307 | Inert |
| $O_2$ | 1.75 | 1.75 |
| Total % | 100 | 100 |

In a 0.5" stainless steel reactor, 7.0 cc of catalyst was charged with an inert diluent and processed with a feed consisting of 0.65 vol % propane, 1.75 vol % oxygen, and 26 vol % steam (balance was nitrogen). The feed was processed over the catalyst at 1.4 sec residence time and atmospheric pressure. Temperatures were increased to achieve desired conversion. Gas and liquid products were collected and analyzed by gas chromatography (GC).

Results for the five runs, operated at a reaction temperature range of 350-400° C., are summarized in Table 2 below:

TABLE 2

| | Finishing reactor results | | | | | |
|---|---|---|---|---|---|---|
| | Bed Temp, ° C. | Pressure, psig | Res. Time, sec. | Propane conv., % | AA yield, % | $CO_x$ yield, % |
| Example 1 | 356 | 0 | 1.4 | 36.3 | 29.6 | 3.8 |
| Example 2 | 366 | 0 | 1.4 | 43.4 | 35.8 | 4.4 |
| Example 3 | 377 | 0 | 1.4 | 56.3 | 45.5 | 6.2 |
| Example 4 | 388 | 0 | 1.4 | 64.2 | 49.1 | 10.1 |
| Example 5 | 400 | 0 | 1.4 | 71.5 | 51.3 | 14.9 |

The data above surprisingly demonstrate that a yield of up to about 50% of acrylic acid can be obtained by processing an AOG feed containing a low concentration of propane in the finishing reactor. In addition, use of the finishing reactor reduces the load on the thermal oxidizer, as compared to the current commercial process, as the primary by-product of the finishing reactor is $CO_x$.

COMPARATIVE EXPERIMENTS 6-7

Single-Stage Operation for Propylene Conversion

In a 0.5" stainless steel reactor, 4.0 cc of the catalyst of Examples 1-5 was charged without a diluent. A feed consisting of 4.9% propylene, 2.1% propane, 14.7% oxygen, and 23% steam (balance nitrogen) was processed over the catalyst at 3 sec residence time and atmospheric pressure. The reactor temperature was adjusted to consistently achieve >99% propylene conversion; gas and liquid products were collected and analyzed by GC. The preceding procedure was done twice at different temperatures and the results are shown in Table 3. No finishing reactor was used.

EXAMPLES 8-11

Single-Stage Operation with Finishing Reactor

The procedure of Comparative Experiments 6 and 7 was repeated at similar conditions, except that a finishing reactor was added in series to the system. The temperature in the first reactor was adjusted to achieve >99% propylene conversion and the gaseous off-gas stream was processed in the finishing reactor at temperatures required to give >65% propane conversion. Products were analyzed by GC.

The data obtained are given in Table 3.

TABLE 3

| | 1st reactor temp, °C. | Finishing reactor temp, °C. | Propylene conversion, % | Propane conversion, % | Oxygen conversion, % | Acrylic acid yield, % |
|---|---|---|---|---|---|---|
| Comparative Example 6 | 337 | n/a | 99.3 | 24.2 | 61.7 | 65.8 |
| Comparative Example 7 | 341 | n/a | 99.6 | 32.1 | 66.1 | 66.7 |
| Example 8 | 334 | 335 | 99.9 | 64.4 | 74.6 | 75.4 |
| Example 9 | 340 | 348 | 100.0 | 71.1 | 77.2 | 76.6 |
| Example 10 | 336 | 345 | 100.0 | 65.4 | 74.4 | 73.9 |
| Example 11 | 336 | 351 | 99.1 | 72.2 | 76.6 | 74.2 |

The data in Table 3 show that when using a mixed propylene/propane stream, the first reactor/finishing reactor/same catalyst configuration is able to give a higher acrylic acid yield from the feedstock than the first reactor alone. In addition, a first reactor-only process converted most of the propylene, but only converted less than one-third of the available feed propane. Attempts to achieve higher propane conversion in a first reactor-only process resulted in runaway reactor temperatures and excessive $CO_x$ yields.

The first reactor/finishing reactor/same catalyst process increased AA yields significantly by allowing for reactive separation of the propylene in the first reactor followed by significant processing of the propane in the finishing reactor.

What is claimed is:

1. A process comprising:
   (A) contacting a gas comprising oxygen, propane and propylene with at least one catalyst under reaction conditions sufficient to at least partially convert the propylene into a final product comprising acrylic acid;
   wherein step (A) comprises:
   (a1) contacting the gas with a first catalyst under reaction conditions sufficient to at least partially convert the propylene into acrolein and to produce a gas phase intermediate product comprising acrolein; and
   (a2) contacting at least part of the acrolein-containing gas phase intermediate product of step (a1) with oxygen and a second catalyst under reaction conditions sufficient to at least partially convert the acrolein into a final product comprising acrylic acid;
   (B) feeding said final product to a separation column, in which the final product is split into a liquid stream, which is rich in acrylic acid, and a gaseous by-product stream comprising propane and propylene in a volume ratio of from 99.9:0.1 to 95:5;
   (C) contacting the gaseous by-product stream with oxygen in the presence of a Mo/V/Te/Nb mixed metal oxide catalyst in a finishing reactor under reaction conditions sufficient to at least partially convert propane to acrylic acid, wherein the feed gas to the finishing reactor comprises propane in an amount between 0.1 vol % and 8 vol %, oxygen in an amount between 1 vol % and 50 vol %, and water in an amount between 1 vol % and 50 vol %, based upon the total volume of the gaseous by-product stream.

2. The process of claim 1 wherein at least one additional gas phase stream comprising propane is fed to step (C).

3. The process of claim 1 where the contacting of step (C) is conducted in a fixed bed reactor.

4. The process of claim 1 wherein at least one catalyst is a Mo/V/Te/Nb mixed metal oxide.

5. The process of claim 1 wherein catalyst in step (A) and the catalyst in step (C) are substantially the same.

6. The process of claim 1 wherein the temperature of the contacting in step (C) is from 0 to 500° C.

7. The process of claim 1 wherein the pressure of the contacting in step (C) is from 0 to 791 kPa gauge.

8. The process of claim 1 wherein the catalysts in steps (a1), (a2) and (C) are all different.

9. The process of claim 1 wherein the feed gas to the finishing reactor comprises propane in an amount between 0.1 vol % and 1 vol %.

10. The process of claim 1 wherein the feed gas to the finishing reactor comprises propane in an amount between 0.1 vol % and 0.7 vol %.

11. The process of claim 1 wherein the feed gas to the finishing reactor comprises propane in an amount between 0.1 vol % and 0.65 vol %.

* * * * *